United States Patent [19]
Trotta

[11] Patent Number: 5,342,386
[45] Date of Patent: Aug. 30, 1994

[54] CATHETER WITH MULTIPLE FLEXIBILITIES ALONG THE SHAFT

[75] Inventor: Thomas Trotta, Miami, Fla.
[73] Assignee: Cordis Corporation, Miami Lakes, Fla.
[21] Appl. No.: 967,520
[22] Filed: Oct. 26, 1992
[51] Int. Cl.$^5$ ............................................ A61M 25/00
[52] U.S. Cl. .................................... 606/194; 604/96; 604/280
[58] Field of Search ............... 604/43, 96, 280, 282; 606/192, 194

[56] References Cited

U.S. PATENT DOCUMENTS

| | | | |
|---|---|---|---|
| Re. 32,983 | 7/1989 | Levy | 428/36.92 |
| 3,733,309 | 5/1973 | Wyeth et al. | 260/75 T |
| 4,100,309 | 7/1978 | Micklus et al. | 427/2 |
| 4,119,094 | 10/1978 | Micklus et al. | 128/132 R |
| 4,323,071 | 4/1982 | Simpson et al. | 128/343 |
| 4,356,300 | 10/1982 | Isler et al. | 528/324 |
| 4,411,055 | 10/1983 | Simpson et al. | 29/447 |
| 4,456,000 | 6/1984 | Schjeldahl et al. | 128/1 D |
| 4,490,421 | 12/1984 | Levy | 428/35 |
| 4,563,181 | 1/1986 | Wijayarathna et al. | 604/280 |
| 4,743,258 | 5/1988 | Ikeda et al. | 623/1 |
| 4,820,349 | 4/1989 | Saab | 128/344 |
| 4,835,003 | 5/1989 | Becker et al. | 427/2 |
| 4,846,174 | 7/1989 | Willard et al. | 604/96 |
| 4,886,506 | 12/1989 | Lovgren et al. | 604/280 |
| 4,898,591 | 2/1990 | Jang et al. | 604/282 |
| 4,906,244 | 3/1990 | Pinchuk et al. | 606/194 |
| 4,917,667 | 4/1990 | Jackson | 604/96 |
| 4,950,257 | 8/1990 | Hibbs et al. | 604/265 |
| 4,976,690 | 12/1990 | Solar et al. | 604/96 |
| 5,032,113 | 7/1991 | Burns | 604/96 |
| 5,047,045 | 9/1991 | Arney et al. | 604/96 |
| 5,108,415 | 4/1992 | Pinchuk et al. | 606/194 |
| 5,163,431 | 11/1992 | Griep | 604/282 |
| 5,234,416 | 8/1993 | Macaulay et al. | 604/282 |

FOREIGN PATENT DOCUMENTS

| | | |
|---|---|---|
| 274411 | 7/1988 | European Pat. Off. . |
| 2011307 | 7/1979 | United Kingdom . |
| 1600963 | 10/1981 | United Kingdom . |

OTHER PUBLICATIONS

USCI The Innovation Continues . . . PE Plus II.
Farrissey et al, "Polyamide Thermoplastic Elastomers", Chapter 8, *Handbook of Thermoplastic Elastomers*, pp. 258, 259.
Grilon Grilamid EMS Technical Data Sheet.

Primary Examiner—John D. Yasko
Assistant Examiner—Anthony Gutowski
Attorney, Agent, or Firm—Lockwood, Alex, Fitzgibbon & Cummings

[57] ABSTRACT

Catheters are provided which have multiple flexibilities along their shafts as well as high pressure capabilities throughout the length of the catheter. Included is a catheter body having a relatively high stiffness which is particularly well-suited for maximum pushability through a body cavity or vessel. Secured to the distal end portion of this catheter body is a thin-walled, flexible tube which exhibits low stiffness to thereby impart maximum flexibility to the distal or tip portion of the catheter. A medical device balloon or other distal end member such as an atraumatic tip is secured to the distal end portion of the connecting tube. In the preferred arrangement, the thin-walled, flexible tube had been constructed by proceeding with radial expansion method in order to impart characteristics of excellent flexibility and high burst strength to the thin-walled flexible tube and thus to the assembled catheter.

11 Claims, 1 Drawing Sheet

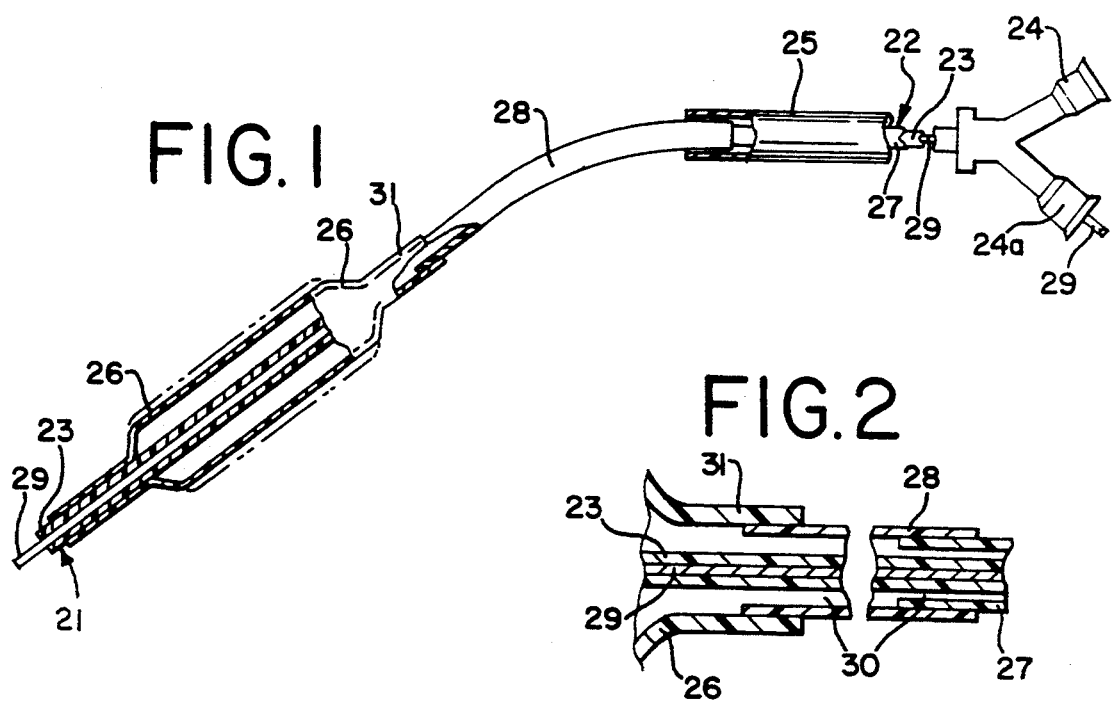
FIG. 1
FIG. 2
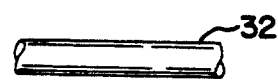
FIG. 3a
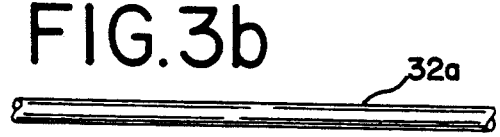
FIG. 3b
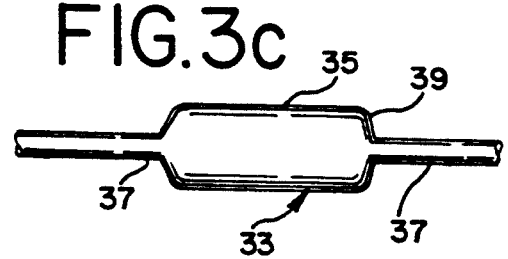
FIG. 3c
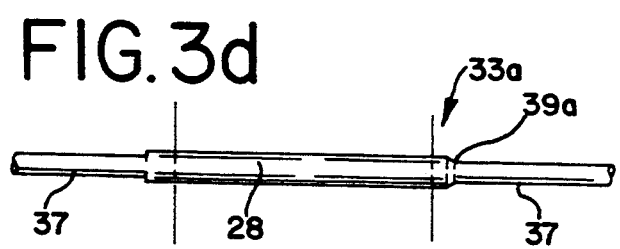
FIG. 3d

CATHETER WITH MULTIPLE FLEXIBILITIES ALONG THE SHAFT

BACKGROUND AND DESCRIPTION OF THE INVENTION

The present invention generally relates to medical device catheters, as well as to processes for making same. More particularly, the invention relates to medical devices in the form of catheters that exhibit varying flexibility along the length of the catheter shaft while simultaneously exhibiting high pressure capabilities throughout the length of the catheter. A portion of the catheter shaft which is positioned generally distally therealong is particularly thin-walled and flexible when compared with the rest of the catheter shaft. This thin-walled and flexible component has an exceptionally high burst strength and is prepared by a procedure which includes radially expanding a parison. Exemplary catheters include so-called balloon catheters such as those designed for angioplasty, valvuloplasty, urological uses and the like.

Various types of catheters are used for different types of medical applications. In several instances, the catheters must wind their way through curved and/or branched body passageways or vessels, necessitating a catheter body that is flexible while still exhibiting adequate stiffness to supply torque properties which enable the catheter to be fed and maneuvered without kinking or excessive twisting which will hamper proper movement through the body cavity or vessel. At the same time, flexibility, particularly at the distal end or lead portion of the catheter should be provided in order to present bending attributes whereby the distal portion of the catheter can be more easily guided into branching passageways or more readily follow tortuous pathways of body vessels or cavities. Numerous approaches have been taken in attempting to achieve the desired combination of adequate torque and flexibility. Some include the addition of mechanical components such as coiled wires. Others seek to provide polymers which exhibit a compromise between competing desired attributes, at times in connection with specific types of catheters. Still other approaches incorporate treatments of catheter bodies or shafts in an effort to provide desired properties.

Some of these approaches are not particularly suitable when the body passageway is especially narrow and/or when the catheter body or shaft must provide a threshold burst strength which is needed for delivering fluids through the catheter body or shaft. Typical medical device catheters of this type require both thinness and exceptional wall strength while still being maneuverable through narrow, curved pathways or branches. These types of catheters include those which must pass through narrow, branched blood vessels in order to deliver pressurized fluid to a location within the body. A particular type of catheter in this regard delivers pressurized fluid to a balloon component at a distal portion of the catheter. Balloon components of this type, when filled with the pressurized fluid will distend or increase in radial size, typically in order to compact or reduce the size of a lesion which has developed in a diseased body cavity such as a blood vessel. An exemplary procedure in this regard is known as percutaneous transluminal coronary angioplasty, and catheters especially designed to carry out this procedure are known as percutaneous transluminal coronary angioplasty (PTCA) catheters.

The typical PTCA catheter utilizes an outer body or shaft having a single flexibility designed to provide a compromise in performance characteristics. The compromise involves a target flexibility that provides some aspects, but not necessarily the ideal aspects, of having a distal end which is flexible to conform to the anatomy while being stiff enough in the proximal end to be pushable, and at the same time being able to withstand the required fluid pressures to inflate the balloon. By proceeding in accordance with the present invention, there is no need to attempt to attain these compromises. The proximal shaft of an outer catheter assembly is as stiff as desired for maximum pushability and strength, while a distal section which is particularly thin and flexible imparts minimal stiffness and exceptional strength to the distal portion of the outer catheter assembly. In the preferred embodiment, stiffness of this distal portion is controlled by an inner tube or shaft which is coaxial with the outer catheter assembly.

In summary, the medical device catheter has a shaft or catheter body composed of an elongated tube having a selected, relatively great stiffness. A thin-walled flexible tube is secured to the distal end of the elongated, stiff catheter body. This thin-walled flexible tube has a stiffness substantially less than that of the elongated catheter body, and its thin-walled and flexible characteristics preferably are developed, at least in part, by a procedure wherein the thin-walled, flexible tube is made from a parison that is radially expanded. In the preferred embodiment, this thin-walled flexible tube connects the distal end of the elongated, stiff catheter body with a tip member such as the proximal end portion of a medical device balloon having a non-distended, collapsed profile which expands to a distended profile upon the application of high fluid pressure through the elongated catheter, including the thin-walled flexible tube, which although being exceptionally flexible is also exceptionally high in burst strength so as to be adequate to withstand the high pressure of the fluid therewithin.

It is a general object of the present invention to provide an improved medical device catheter having multiple flexibilities along its shaft while simultaneously exhibiting high pressure capabilities.

Another object of this invention is to provide an improved percutaneous transluminal coronary angioplasty catheter that is especially well-suited to follow bends and branches within blood vessels and the like while still possessing burst strength adequate to withstand the high pressures needed for angioplasty procedures.

Another object of the present invention is to provide an improved outer tube assembly for coaxial catheters, which outer tube assembly exhibits multiple flexibilities including minimal flexibility at a distal portion location whereby distal stiffness is controlled by the inner, coaxial tube.

Another object of this invention is to provide an improved coaxial catheter having an inner tube or body which accommodates a guidewire and provides distal stiffness to the outer coaxial tube having a unique section of minimal stiffness and maximum flexibility.

Another object of this invention is to provide an improved catheter having a distal portion section which is of minimal stiffness and of high burst strength by preparing same from a parison that is radially expanded.

Another object of the present invention is provide an improved medical device balloon catheter incorporating a section of minimal stiffness and maximum flexibility in order to provide a balloon catheter having a portion immediately proximal to the balloon which allows the balloon to easily follows bends and branches within body cavities or vessels.

These and other objects, features and advantages of the present invention will be clearly understood through a consideration of the detailed description.

BRIEF DESCRIPTION OF THE DRAWINGS

In the course of this description, reference will be made to the attached drawings, wherein:

FIG. 1 is an elevational view, partially in cross-section, of a catheter incorporating the present invention;

FIG. 2 is an enlarged cross-section, partially broken away, of portions of the catheter illustrated in FIG. 1; and FIGS. 3a, 3b, 3c and 3d are elevational illustrations of tubing as it is progressively processed to transform same into the thin-walled, flexible tube which is a component of the catheters made in accordance with the invention.

DESCRIPTION OF THE PARTICULAR EMBODIMENTS

A catheter illustrative of the type of medical device suitable for employment of the present invention is illustrated in FIG. 1. The particular illustrated catheter is one designed for percutaneous transluminal coronary angioplasty procedures, and it is of a so-called coaxial design. An inner tube, generally designated as 21 is coaxially positioned within an outer tube assembly, generally designated as 22, in accordance with generally known practices. Conventional inner tube 21 includes an elongated shaft 23 which provides a passageway for a guidewire 29.

Coaxially positioned over the inner tube 21 is the outer tube assembly 22 which includes a medical device balloon member 26, the outer tube assembly 22 providing a passageway for controlling the inflation and deflation of the medical device balloon member 26. A suitable branched connector of known construction having branches 24 and 24a facilitates manipulation of the guidewire 29 and linkage to a known device for passing pressurized inflation fluid, such as saline solution, into and through the catheter and into the medical device balloon member 26 when it is desired to inflate the balloon member 26. A guiding catheter 25 is also illustrated in a typical position as it is used in connection with the invention.

With more particular reference to the outer tube assembly 22, in addition to the branched connector and the medical device balloon member 26, this assembly further includes an elongated catheter body shaft or tube 27 and a thin-walled, flexible tube 28. In the illustrated embodiment, the thin-walled, flexible tube 28 serves as a connecting shaft between the elongated body shaft or tube 27 and the medical device balloon 26. It could also be used as a connection to other tip members which do not include a balloon. It will be appreciated that the thin-walled, flexible tube 28 is positioned distally of the elongated body shaft or tube 27.

In an important aspect of this invention, the thin-walled flexible tube 28 imparts minimal stiffness to the tip or distal end portion of the catheter assembly while also providing it with exceptional burst strength. Because of the minimal stiffness imparted by the thin-walled flexible tube 28, the stiffness of the tip or distal end portion of the catheter assembly is controlled by the material of the inner tube 21 which is coaxially positioned within the thin-walled flexible tube 28 when the outer tube assembly 22 is guided through the pathway within the body passageways or vessels which is mapped out by the guidewire 29. The distal end portion of the balloon member 26 or other tip member is secured such as by heat sealing, adhesive or the like to the distal end portion of the inner tube 21. Because of this exceptional flexibility of the thin-walled flexible tube 28 at the distal location at which bending is extremely important, the elongated body shaft 27 can be designed to be as stiff as desired for maximum pushability and strength.

Elongated body shaft 27 has a stiffness substantially greater than the minimal stiffness of the thin-walled flexible tube 28. A typical minimum flexural modulus is on the order of about 100,000 psi. Burst pressure will be at least about 200 psi, preferably at least about 400 psi. When the catheter assembly is of the PTCA type, the wall thickness of the extruded polymer elongated body shaft 27 will range between about 0.002 inch and about 0.006 inch. After extrusion and annealing, shaft 27 typically has a yield point of greater than 3400 psi.

One or more thin-walled flexible tubes 28 are provided, although in most typical applications, only one is needed or desired. Tube 28 has a wall thickness of not substantially greater than about 0.0005 inch or less. Despite this wall thinness, tube 28 possesses a burst pressure of at least about 400 psi. When normalized, its yield point is significantly greater than that of the elongated body shaft 27. Tube 28 has a yield point exceeding 20,000 psi. For example, a typical normalized yield point for a suitable thin-walled flexible tube 28 is about 23,000 psi, while that of a suitable elongated body shaft 27 is about 5050 psi.

As can perhaps be best seen in FIG. 2, in the illustrated preferred embodiment, the proximal end of the thin-walled flexible tube 28 is secured to the distal end portion of the elongated body shaft 27, and the distal end portion of the thin-walled flexible tube 28 is secured to a proximal end portion or leg 31 of the medical device balloon member 26 or other tip member. While any suitable assembly method could be utilized such as those incorporating adhesives, preferred assembly is accomplished by energy application such as known heat sealing techniques. In a typical percutaneous transluminal coronary angioplasty catheter, thin-walled flexible tube 28 would have a length on the order of 10 inches (25 cm), and the elongated body shaft 27 would have a length on the order of about 90 inches (about 229 cm). Fluid passes through the catheter assembly along passageway 30 between the inner tube 21 and the outer tube assembly 22, necessitating the high burst strength exhibited by the thin-walled flexible tube 28.

A tube which is only radially expanded would provide tubing having adequate strength. The preferred tubing is made from double-stretched tubing, primarily for cosmetic reasons, wherein the tubing is axially stretched twice.

When the double-stretched approach is desired, thin-walled, flexible tube 28 is constructed from a parison that has been axially elongated and radially expanded. It is especially preferred that the tube 28 be made of a nylon or of a polyamide material. It has been determined that thin-walled flexible tubes 28 made from nylon or polyamide parisons subjected to radial expansion provide tubes 28 that exhibit the advantageous combination of thin-walled flexibility with superior burst strength.

FIGS. 3a through 3d illustrate the procedure by which a double-stretched, thin-walled flexible tube 28 is formed. A length of tubing or parison 32 shown in FIG. 3a is subjected to axial elongation to form an elongated tubing 32a which is stretched to achieve an elongation of between about 250% and about 300% of the original length of the parison 32. The stretching may be omitted. Whether included or not, the elongated tubing 32a is subjected to radial expansion by applying fluid pressure to the inner lumen thereof. Typically, the elongated tubing 32 is allowed to expand to a "free-blown" diameter wherein no mold is used to restrict its expansion. If it is desired to very carefully control the step illustrated in FIG. 3c, same could be accomplished within a mold having a shape generally approximating that of the radially expanded elongated tubing, generally designated as 33 as depicted in FIG. 3c. Included is an expanded portion 35, leg portions 37, and expansion end walls 39. Preferably, and typically practiced under a free-blown situation, the elongated tubing 32a is first kinked to initiate a bubble, and the free-blown balloon propagates from that initiation site upon application of the fluid pressure to develop the radial expansion. Preferably, the expansion is at least about 200%. Generally speaking, this procedure can be characterized as a "pre-blow" step. When double-stretching is desired, and as illustrated in FIG. 3d, the radially expanded elongated tubing 33 is axially stretched or elongated in order to form an axially stretched or re-stretched radially expanded elongated tubing 33a. This axial stretch will be a stretch of between about 30 and about 80% beyond the length of the radially expanded tubing 33, during which there is a significant reduction in the expansion end walls 39 to provide reduced-size expansion end walls 39a.

Thereafter, the radially expanded elongated tubing 33a is subjected to heat setting conditions. A preferred manner of accomplishing the heat set to the section 39a is within a mold that has an internal diameter corresponding to the desired external or outer diameter of the thin-walled flexible tube 28. Heat set is achieved by pressurizing tube 33a and then subjecting it to heating for a short period of time while within the heat set mold. This is followed by a brief cooling period. Thin-walled flexible tube 28 is removed from the tube 33a, typically by severing along severance lines as generally illustrated by the pair of center lines in FIG. 3d.

Medical device balloon member 26 preferably is prepared from a nylon or from a polyamide parison which is subjected to processing similar to that preferably practiced to form the thin-walled flexible tube 28. The initially provided parison is stretched axially to about 150% and up to about 200% of the initial parison length. The thus elongated parison is subjected to radial expansion by initiating a small bubble and placing same within a pre-blow mold to provide a radial expansion to form a structure as generally illustrated in FIG. 3c. A second axial elongation is then accomplished by a second stretching of about 40% to about 80% beyond the length of the radially expanded tube. The second-stretched tubing is then placed within a mold chamber to form the desired balloon shape. Heat setting is also preferably accomplished in order to provide the medical device balloon member 26.

With more particular reference to the material out of which the outer tube assembly 22 and especially the thin-walled flexible tube 28 is made, same should be a thermoforming plastic. Such a material can be heated to a temperature below its melting point and deformed or formed to take on another shape and/or size. When cooled, these types of materials retain that new shape and/or size, and this procedure is substantially repeatable. When heat set, these materials become thermoformed to the desired geometry of the finished component, subject to re-forming if heated beyond a predetermined elevated temperature for the particular material. Details of these materials as well as of procedures and devices for shaping and conditioning same are found, for example, in U.S. Pat. Nos. 4,906,244, 4,938,676, 5,017,325, 5,055,024 and 5,108,415, the subject matter thereof being incorporated by reference hereinto.

Thin-walled flexible tube 28 is to be made of materials that have substantial tensile strength, are resistant to the development of pin holes, are generally scratch-resistant, and possess reasonably good moisture resistance. Nylon materials and/or polyamide materials are typically suitable. Materials of the Nylon 12 type have been found to possess these advantageous properties. Other exemplary nylons include Nylon 9, Nylon 11, Nylon 66, Nylon 69 and other polyamides. Polyamides include nylons, polyetheramides and polyetheramides blended with another polyamide-type of material. Polyetheramide is a polyamide elastomer having substantially no ester linkages. The polyetheramides can be blended with materials having polyamide structures per se as well as certain polyesteretheramides.

Polyetheramide components can be generally categorized as polyamide elastomers, and they have been found to possess properties that are especially exceptional for short dwell time medical devices. They have been found to offer a high strength to flexibility ratio and do not exhibit blooming of particles upon aging. Polyetheramides can be blended with other polyamide types of materials in order to greatly extend the flexibility range while retaining the advantageous properties of the polyetheramide material. It has been found that, when certain of these polyamide-types of materials are blended with a polyetheramide, the result is a polymer blend which, when extruded, enjoys the properties of good flexibility while maintaining an extremely high burst strength to flexibility ratio and while exhibiting bloom retardation properties which persist even upon substantial aging.

The polyetheramides (PEA or PETA) include polyamide elastomers in which there are virtually no ester linkages in that the bonds between the hard and soft segments are amides. These materials are also free from monomeric plasticizers, and they have a high hydrolysis stability. Exemplary materials in this regard are available from EMS-Chemie AG or Emser Industries. Exemplary trade designations are Grilamid and Grilon. Polyetheramides typically are prepared by directly reacting an amine-terminated soft segment with a dimer acid and caprolactam. As an example in this regard, when the amine-terminated soft segment is bis(3-aminopropyl)polyoxytetramethylene glycol, and when the dimer acid is an acid such as EMPOL 1010, a PEA or PETA polymer of the following structure is formed:

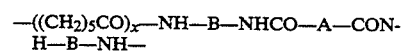

wherein A designates dimer acid segments, B designates

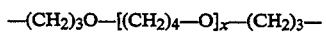

and x is an integer greater than 1. It will be noted that these formulas contain no ester linkages.

When it is desired to blend polyetheramide materials of this general type with the other polyamide-types of materials, this polyetheramide having substantially no ester linkages will be present at between about 10 and about 90 percent by weight, based upon the total weight of the polymer blend. Typically any such blend will include between about 10 and about 90 percent by weight, based upon the total weight of the polymer blend, of a flexibility modifying polyamide type of material.

With more particular reference to the flexibility modifying polyamide-types of material, they can typically fall into two different categories, one being a polyamide per se, and the other being a polyesteretheramide. Both have been found to increase the flexibility of the polyetheramide, which may not be particularly preferred for the thin-walled flexible tube 28. Polyamides include the nylons such as Nylon 6, Nylon 11, Nylon 12 and the like as well as materials such as Grilamid L25. The general structure of these types of polyamides is, of course, quite well known, the structure having recurring polyamide groups (—CONH—) as an integral part of the polymer chain. The typical polyamide is a high molecular weight polymer in which these amide linkages occur along the molecular chain. Polyesteretheramides, unlike the polyetheramides, typically do have ester linkages, believed to contribute significantly to the blooming phenomenon. Included are the PEBA materials, namely the polyether block amide or ester-linked polyether-polyamide copolymer materials, which are believed to have a structure as follows:

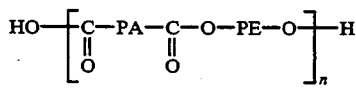

wherein PA is a polyamide, PE is a polyether, and n is an integer greater than 1 which represents the number of blocks of copolymer molecular units within the molecular formula of the copolymer. Representative polyesteretheramide materials include the Pebax polymers. It has been found that, when the Pebax polymers are utilized, the bloom retardation characteristic is accomplished when the shore hardness is equal to or harder than Shore 70D.

With further reference to the aspect of the present invention wherein blooming or migration of monomers to the surface is retarded, this feature is particularly advantageous in those instances where a coating is applied, such as a hydrogel coating, to the extruded polymer tubing, especially to the thin-walled tube 28. It has been found that such blooming undermines coatings which are applied. Exemplary coating materials are hydrogel materials that are copolymers of polyurethane and polyvinylpyrrolidone or cross-linked copolymers of polyethylene oxide and polyhydroxyethyl methacrylate. Exemplary hydrogel coatings are available from Hydromer Inc. under the registered trademark HYDROMER and are illustrated in Miklus et al. U.S. Pat. No. 4,100,309, incorporated by reference hereinto. Hydrophilic coatings having low friction properties are described, for example, in Lambert U.S. Pat. No. 4,585,666 and Becker et al. U.S. Pat. No. 4,835,003, incorporated by reference hereinto.

The following examples illustrate preferred embodiments concerning the invention.

EXAMPLE

Elongated Proximal Body Shaft

An elongated body shaft 27 was produced with a typical commercial extruder (a Killion ¾ inch extruder) from EMS Grilamid TR55 nylon, clear. The resultant tubing had an outer diameter of 0.0435 inch and an inner diameter of 0.0375 inch. The tubing was annealed at 150° C. for thirty minutes. Pressure testing on five extruded and annealed tubes showed an average burst pressure of 748 psi, the standard deviation being 30.1, which when normalized, equals a yield point of 5050 psi. The literature value for the flexural modulus of this material is 296,000 psi.

Thin-Walled Flexible Distal Tube

A parison of Huls Vestamid L2101F (a Nylon 12) was produced on conventional extrusion equipment, the parison having an outer diameter of 0.0134 inch and an inner diameter of 0.0065 inch. The parison was axially stretched in a first stretching operation to between 250 and 300% of the initial parison length. Radial expansion was performed by first pressurizing the inner lumen of the first stretched parison to 790 psi, then allowing the elongated parison to expand to a "free-blown" diameter, there being no mold utilized to restrict expansion. The elongated parison was first kinked to initiate a bubble, and the free-blown radial expansion volume propagated from that initiation site in order to provide a pre-blown intermediate. This pre-blown intermediate was subjected to a second stretching step in order to axially elongate it by 30 to 80%. The twice-stretched tubing was heat set within a heat set mold that is a hypotube having an internal diameter of 0.042 inch and an outer diameter of 0.058 inch, the hypotube being housed in a circulating jacket that allows either hot fluid or cold fluid to flow around it without directly contacting the tubing being heat set. The heat set was achieved by pressurizing the tube to 275 psi and subjecting it to 140° C. for thirty-six seconds while within the hypotube. After the heat set period, the tubing was cooled for thirty-six seconds at approximately 20° C. The resulting thin-walled flexible tube had an outer diameter at 100 psi of 0.0420 inch. An average wall thickness of five such prepared tubes was 0.0005 inch. Each tube was 25 cm in length, and the average burst pressure of the tubing was 542 psi, standard deviation of 32.5. When normalized, this average burst pressure defines a yield point of 23,000 psi.

Medical Device Balloon

High pressure medical device balloon members 26 were prepared from Huls Vestamid L2101F (a Nylon 12) from an extruded parison having an outer diameter of 0.032 inch and an inner diameter of 0.019 inch. A medical device balloon member having a balloon profile of 3.0 mm was made by the following procedure. The parison was stretched axially 150 to 200% in a first stretch step. A small bubble was initiated using a short burst of heated air while the parison was pressurized. This tubing was placed into a pre-blow mold (0.088 inch diameter by 2.5 inches in length) and pressurized to 630 psi. This achieved a first radial expansion and provided a balloon portion approximately 0.88 inch in diameter and 2.5 inches in length. A second stretch was then conducted to elongate 40% to 80%. The second stretched tubing was then placed into a forming mold in order to finish formation of the balloon to the desired final shape. Heat setting was then conducted within this same mold under elevated pressure and temperature, the heat set time being 36 seconds. Cooling was then conducted for thirty-six seconds. The resulting medical device balloon had an average outer diameter (at 100 psi) of 0.116 inch, and an average burst pressure of 351 psi, standard deviation of 15.

It will be understood that the embodiments of the present invention which have been described are illustrative of some of the applications of the principles of the present invention. Numerous modifications may be made by those skilled in the art without departing from the true spirit and scope of the invention.

I claim:

1. A medical device balloon catheter comprising:

a catheter body which is an elongated tube having a given stiffness, said catheter body having a proximal end and a distal end;

a medical device balloon member with a balloon portion having a non-distended, collapsed profile and a distended, expanded profile which develops upon the application of fluid pressure internally of the balloon, said balloon member having a proximal end leg portion and a distal end leg portion which do not expand upon said application of fluid pressure internally of the balloon;

a thin-walled, flexible connecting tube which exhibits neither the collapsed profile nor the expanded profile that develops in the medical device balloon member of the catheter, said connecting tube being secured between said distal end of the catheter body and said proximal end leg portion of the balloon member, said connecting tube thereby spacing said balloon member from said catheter body, said connecting tube having been radially expanded to impart its thin-walled and flexible characteristics thereto, the connecting tube having a stiffness less than said given stiffness of the catheter body while having a burst pressure of not less than about 400 psi;

said thin-walled flexible connecting tube is made from a polymer selected from the group consisting of nylons, polyamides, polyetheramides and blends of polyetheramides with other polyamide types of materials;

means for manipulating the balloon catheter into and through a body vessel to position the balloon member at a selected location within the body vessel;

means for imparting fluid pressure interiorly of the balloon to distend and expand the balloon member;

an inner tube which is an elongated tube having a proximal end and a distal end, the inner tube being substantially co-axially positioned within said catheter body, said thin-walled, flexible connecting tube, and said medical device balloon member;

said distal end of the inner tube being secured to said distal end leg portion of the balloon member; and said means for imparting fluid pressure internally of the balloon member includes a passageway between the outer surface of said inner tube and the combined inner surfaces of said catheter body, said thin-walled, flexible connecting tube, and said medical device balloon.

2. The medical device balloon catheter in accordance with claim 1, wherein said thin-walled flexible connecting tube had been first axially elongated, thereafter radially expanded, and then axially elongated for a second time.

3. The medical device balloon catheter in accordance with claim 1, wherein said given stiffness of the catheter body corresponds to a flexural modulus of at least about 100,000 psi.

4. The medical device balloon catheter in accordance with claim 1, wherein said thin-walled flexible connecting tube has a wall thickness of on the order of approximately 0.0005 inch.

5. The medical device balloon catheter in accordance with claim 1, wherein the catheter is a percutaneous transluminal coronary angioplasty catheter.

6. The medical device balloon catheter in accordance with claim 1, wherein said thin-walled flexible connecting tube is made from a polymer radially expanded at least about 200%.

7. A medical device balloon catheter comprising:

a catheter body which is an elongated tube having a given stiffness, said catheter body having a proximal end and a distal end;

a medical device balloon member with a balloon portion having a non-distended, collapsed profile and a distended, expanded profile which develops upon the application of fluid pressure internally of the balloon, said balloon member having a proximal end leg portion and a distal end leg portion which do not expand upon said application of fluid pressure internally of the balloon;

a thin-walled, flexible connecting tube which exhibits neither the collapsed profile nor the expanded profile that develops in the medical device balloon member of the catheter, said connecting tube being secured between said distal end of the catheter body and said proximal end leg portion of the balloon member, said connecting tube thereby spacing said balloon member from said catheter body, said connecting tube having a wall thickness on the order of about 0.0005 inch and a burst pressure of not less than about 400 psi, the connecting tube having a stiffness less than said given stiffness of the catheter body;

said thin-walled flexible connecting tube is made from a polymer selected from the group consisting of nylons, polyamides, polyetheramides and blends of polyetheramides with other polyamide types of materials;

means for manipulating the balloon catheter into and through a body vessel to position the balloon member at a selected location within the body vessel;

means for imparting fluid pressure interiorly of the balloon to distend and expand the balloon member;

an inner tue which is an elongated tube having a proximal end and a distal end, the inner tube being substantially co-axially positioned within said catheter body, said thin-walled, flexible connecting tube, and said medical device balloon member;

said distal end of the inner tube being secured to said distal end leg portion of the balloon member; and said means for imparting fluid pressure internally of the balloon member includes a passageway between the outer surface of said inner tube and the combined inner surfaces of said catheter body, said thin-walled, flexible connecting tube, and said medical device balloon.

8. The medical device balloon catheter in accordance with claim 7, wherein said given stiffness of the catheter body corresponds to a flexural modulus of at least about 100,000 psi.

9. A medical device catheter comprising:
- a catheter body which is an elongated tube having a given stiffness, said catheter body having a proximal end and a distal end;
- a distal tip member having properties suitable for the leading portion of a medical device catheter;
- a thin-walled, flexible connecting tube which neither collapses nor expands during use of the catheter, said connecting tube being secured between said distal end of the catheter body and said distal tip member, said connecting tube thereby spacing said distal tip member from said catheter body, said connecting tube having a wall thickness on the order of about 0.0005 inch and a burst pressure of not less than about 400 psi, the connecting tubing having a stiffness less than said given stiffness of the catheter body;
- said thin-walled flexible connecting tube is made from a polymer selected from the group consisting of nylons, polyamides, polyetheramides and blends of polyetheramides with other polyamide types of materials;
- means for manipulating the catheter into and through a body vessel to position the distal tip at a selected location within the body vessel;
- an inner tube which is an elongated tube having a proximal end and a distal end, the inner tube being substantially co-axially positioned within said catheter body, said thin-walled, flexible connecting tube, and said distal tip member;
- said distal end of the inner tube being secured to said distal tip member; and
- a passageway between the outer surface of said inner tube and the combined inner surfaces of said catheter body, said thin-walled, flexible connecting tube, and said distal tip member.

10. The medical device catheter in accordance with claim 9, wherein said given stiffness of the catheter body corresponds to a flexural modulus of at least about 100,000 psi.

11. The medical device catheter in accordance with claim 9, wherein said distal tip member is an atraumatic catheter tip.

* * * * *

UNITED STATES PATENT AND TRADEMARK OFFICE
CERTIFICATE OF CORRECTION

PATENT NO. : 5,342,386
DATED : August 30, 1994
INVENTOR(S) : Thomas Trotta

It is certified that error appears in the above-indentified patent and that said Letters Patent is hereby corrected as shown below: On the title page: Item [56]

Under U.S. References Cited, Pat. No. 4,743,258, "Ikeda et al" should read --Ikada et al--.
Col. 3, line 1, "is provide" should read --is to provide--; line 6, "follows" should read --follow--.
Col. 6, lines 61-62, "bis(3-aminopropyl)polyoxytetra-methylene" should read --bis(3-aminopropyl)-poly-oxytetramethylene--.
Col. 10, line 58, "tue" should read --tube--.

Signed and Sealed this

Twenty-sixth Day of September, 1995

Attest:

BRUCE LEHMAN

Attesting Officer     Commissioner of Patents and Trademarks